United States Patent [19]

Kuehnreich

[11] Patent Number: 5,176,624
[45] Date of Patent: Jan. 5, 1993

[54] SHOE BANDAGE

[76] Inventor: Heinz-Peter Kuehnreich, Kirchstrasse 24, 5210 Troisdorf, Fed. Rep. of Germany

[21] Appl. No.: 733,810

[22] Filed: Jul. 22, 1991

[30] Foreign Application Priority Data

Jul. 21, 1990 [DE] Fed. Rep. of Germany ....... 9010863

[51] Int. Cl.⁵ .................... A61F 13/00; A43C 13/00
[52] U.S. Cl. ......................... 602/65; 602/79; 36/110; 36/101; 36/15; 36/50.1; 2/22
[58] Field of Search ........... 2/22; 36/1.5, 2 R, 12, 36/15, 50, 100, 101, 110; 128/892; 602/62, 65, 79

[56] References Cited

U.S. PATENT DOCUMENTS

| 2,236,367 | 3/1941 | Gruber |
| 2,438,711 | 3/1948 | Leach et al. |
| 3,417,408 | 12/1968 | Caggiano |
| 4,166,460 | 9/1979 | Applegate ........................ 602/65 |
| 4,300,294 | 11/1981 | Riecken |
| 4,314,412 | 2/1982 | Anderson et al. |
| 4,575,954 | 3/1986 | Bye |
| 4,773,170 | 9/1988 | Moore et al. |
| 4,852,272 | 8/1989 | Chilewich et al. ............... 36/12 |
| 4,958,447 | 9/1990 | Du Pree ......................... 36/100 |
| 4,969,277 | 11/1990 | Willaims |

FOREIGN PATENT DOCUMENTS 2168234 of 0000 United Kingdom.

Primary Examiner—Paul Prebilic
Attorney, Agent, or Firm—Antonelli, Terry, Stout & Kraus

[57] ABSTRACT

A shoe bandage adapted to be worn over foot bandages, foot injuries or foot wounds. The shoe bandage includes a sole part provided with hook and loop fastening surrounding an outer peripheral edge of the sole part. A one-piece unwindable upper material piece forming an upper shoe part is provided along a lower edge with hook and loop fastening material for enabling an fastening between the lower edge of the upper shoe part and the sole part.

17 Claims, 3 Drawing Sheets

SHOE BANDAGE

FIELD OF THE INVENTION

The present invention relates to a bandage arrangement and, more particularly, to a shoe bandage adapted to be worn over foot bandages or for covering foot injuries or foot wounds.

BACKGROUND OF THE INVENTION

There is a considerable need for shoe bandages in order to facilitate care during a post-operative phase and for constant application in the case of circulatory problems, open spots or sores, and the like especially in geriatrics and severe diabetes. Another need for shoe bandages arises in the protection against cold and as an aid in assisting wheelchair users and assisting rheumatic patients in standing.

As a result of the increasing frequency of vascular surgical operative measures caused by the rising number of aged individuals in the age pyramid as well as ulcers caused by diabetes, coupled with a simultaneous effort to reduce expenses in the medical area, a need has arisen to provide a shoe bandage which ensures a high wearing comfort and enables considerable variability at low manufacturing costs.

SUMMARY OF THE INVENTION

The aim underlying the present invention essentially resides in providing a shoe bandage which ensures a high degree of wearing comfort and which may be manufactured in a simple and inexpensive manner.

In accordance with advantageous features of the present invention, a shoe bandage is provided which includes a sole part having a hook and loop material running around an outer edge and a one-piece unwindable upper material piece, with the material being suitable for hoop and loop connectors along an inner lower edge.

By virtue of a shoe bandage constructed in accordance with the above-noted features of the present invention, due to the separability of the sole part and the upper material piece, with a single sole part and, preferably, also with a single upper material piece, it is possible to ensure utilization as a right or left shoe simply by turning the sole part. This is of considerable importance in determining the necessary tools required as well as the inventory on hand because, generally, such shoe bandages are requested only as individual elements.

In accordance with the present invention, the upper material is shaped symmetrically in a developed view so that the material can be used equally as a left or right shoe bandage.

Alternatively, it is also possible in accordance with the present invention for the upper material part of the shoe bandage to be asymmetrical in shape in a developed view, with the material having the same characteristics on both sides so that it may be used either as a right or left shoe bandage.

In order to facilitate manufacturing, it is advantageous for the upper material to be completely flat in a developed view.

Preferably, in accordance with the present invention, the upper material is unwound from two curved parts with a greater width being provided in a tensioning area, and with the outer edge forming a closed arc that delimits both parts.

According to the present invention, a division of the one-piece upper material can begin at any point along an outside edge that abuts the sole part. However, a division of the one-piece upper material in the heel area is preferable where, as a result of different degrees of overlap when applying the upper material to the sole part, a considerable variation can be achieved in the volume of the closed assembled bandage.

It is also possible in accordance with the present invention to provide an overlapping area laterally inwardly or laterally outwardly whereby, with the same overall surface shape, another form of upper material part results.

In order to achieve yet a further variation in a volume of the assembled shoe bandage, in accordance with the present invention, a cut may be provided extending from an upper edge of the upper material part to a vicinity of the material of the sole, which can be overlapped on the upper material part when applied to the sole part so that a considerable variation in a volume of bandage shoe is possible depending upon a thickness of the foot or a thickness of the bandage.

Preferably, according to the present invention, the cut extending from the upper edge is made in a tensioning area of the shoe bandage.

In accordance with still further features of the present invention, the upper material is capable of a hook and loop connection on an outside of the shoe bandage and, for example, may consist of a material that has loops as well as inside lower edge that cooperates with the hook and loop parts that have hooks. This arrangement makes it possible to close both the heel area and the cuts preferably located in the tensioning area and, preceding from the upper edge, following partial overlapping or covering over with the hook and loop connectors individually. However, other means may be used for ensuring a closure of the shoe bandage and, for example, individual hooks and eyes may be provided on the closed shoe bandage.

In order to enable a variation of the shoe bandage and enable orthopedic adjustment, when assembling the shoe bandage, insert soles and heel wedges may be added, with the sole and heel wedges being exclusively held by the shape of the upper material.

However, the insert soles and heels could also be provided with externally located hook and loop connectors in order to provide a connection to the upper material.

It is also possible in accordance with the present invention, when determining whether the insert will be a right or left shoe bandage, to provide the sole part externally with a slip-resistance shoulder or sole covering which may be simply held in place by, for example, an adhesive.

Depending upon the medical indication or application, it may be advantageous in accordance with the present invention, especially for pressure sensitive points on the foot, to provide cutouts or recesses in the upper material. This approach can affect, in particular, the ankle, the toe area or the heel area. However, in special cases, a hole-shaped cut-out can be provided at any point. These hole-shaped cutouts may, for example, be recesses provided in advance of those which are made by cutting out or cutting off the edges after fitting the shoe to the injured or bandaged foot.

It is also possible in accordance with the present invention to provide individualized stiffening of the upper material. The individualized stiffening may, for example, include areas of a reinforced material sewn or adhesively applied directly to the upper material.

However, it is also possible in accordance with the present invention to provide the individualized stiffening by inserting reinforcing ribs into pockets sewn into the material. The reinforcing ribs may, for example, be flat coil springs.

By virtue of the provision of the individualized stiffening of the upper material, an adjustment of the shoe bandage and application to deformations of the foot can be accomplished in an extremely simple manner.

Advantageously, a cutout area may be provided in the fastening area or, in other words, the edge of the upper material part that abuts the sole, with such area depending upon the tightness or tightening height or thickness of the foot for a given sole length thereby permitting variable adjustment of the upper material to the sole part as well as a subsequent cutting off along the sole edge of any projecting material in the cutout area.

A few different sizes for the individual parts, for example, four parts, are suitable because of the extensive variability of covering all ordinary foot sizes in a satisfactory manner.

The above and other objects, features and advantages of the present invention will become more apparent from the following description when taken in connection with the accompanying drawings which show, for the purpose of illustration only, a shoe bandage constructed in accordance with the present invention.

DETAILED DESCRIPTION

Figure 1:
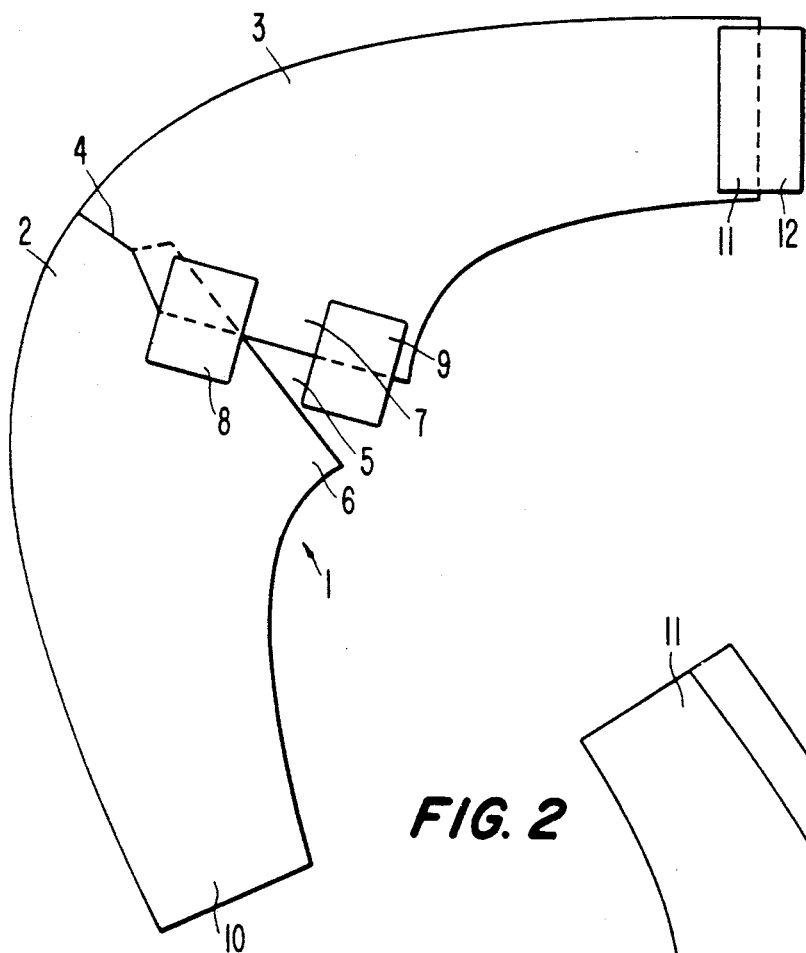
FIG. 1 is a developed view of an outside of an upper material part of a shoe bandage constructed in accordance with the present invention.

Referring now to the drawings wherein like reference numerals are used throughout the various views to designate like parts and, more particularly, to FIG. 1, according to this figure, a shoe bandage constructed in accordance with the present invention comprises a one-piece upper material piece generally designated by the reference numeral 1 of, for example, elastic type bandage material, composed of two flat sickle-shaped material pieces 2, 3 joined at a seam 4 in such a manner that two edges areas 6, 7 of the material pieces 2 partially overlap in a vicinity of a cut 5 in the developed view. Two hook and loop fasteners 8, 9 formed, for example, as VELCRO tabs, are provided in an area of the cut or cutout 5, with the fasteners 8, 9 being fastened to the edge area 7 located above or on the outside of the upper material piece 1. Another hook and loop fastener of, for example, VELCRO, is mounted externally on one of the two rear edges 10, 11. The cut or cutout 5 represents a tensioning area which rear edges 10, 11 form later when overlapping the heel area.

Figure 2:
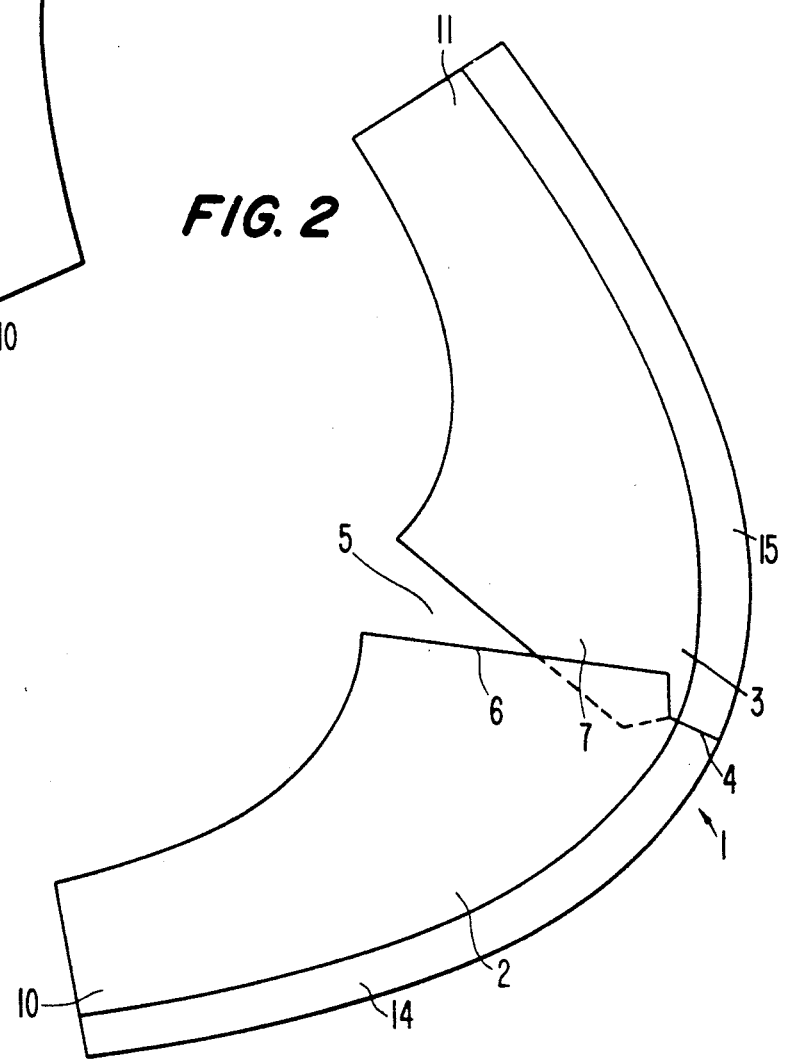
FIG. 2 is a developed view of an upper material part, as viewed from an inside, of a shoe bandage constructed in accordance with the present invention.

As shown in FIG. 2, the part 1 is assembled from the two pieces 2, 3 joined at the seam 4 in such a manner that a cut or cutout 5 is formed, whereby the edge area 6, 7 partially overlap one another. The hook and loop fasteners in the tensioning area are not shown in FIG. 2; however, areas 14, 15 are provided at an inner lower edge of the material pieces 2, 3, with the areas 14, 15 being capable of making hook and loop connections and, for example, being fashioned as strips of a VELCRO material.

Figure 3:
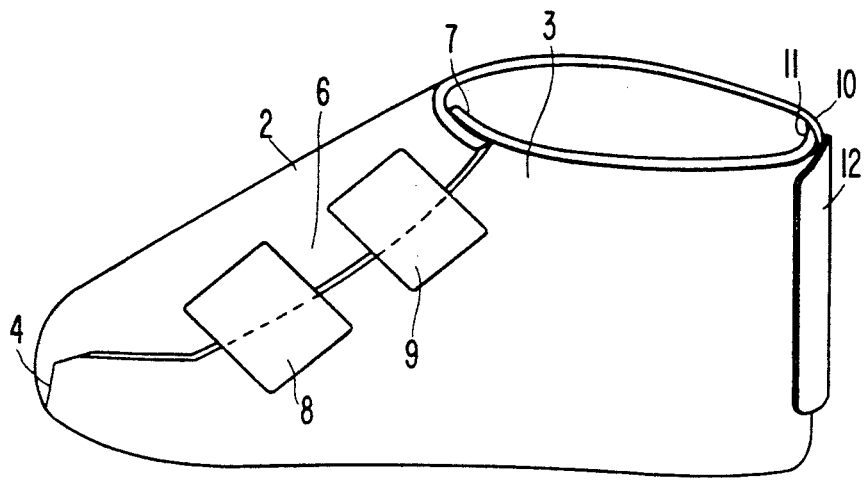
FIG. 3 is a perspective view of an assembled shoe bandage constructed in accordance with the present invention.

The assembled shoe bandage as shown in FIG. 3, includes outer material parts 2, 3 joined together at the seam 4, with the edge area 6 overlapping the edge area 7 in the tensioning area. The areas are connected together by the hook and loop fasteners 8, 9 in a vicinity of the forward edges, while the additional hook and loop connector joins the rear edges 10, 11 in the heel area. The upper material pieces are wrapped around a sole part (not shown).

Figure 4:
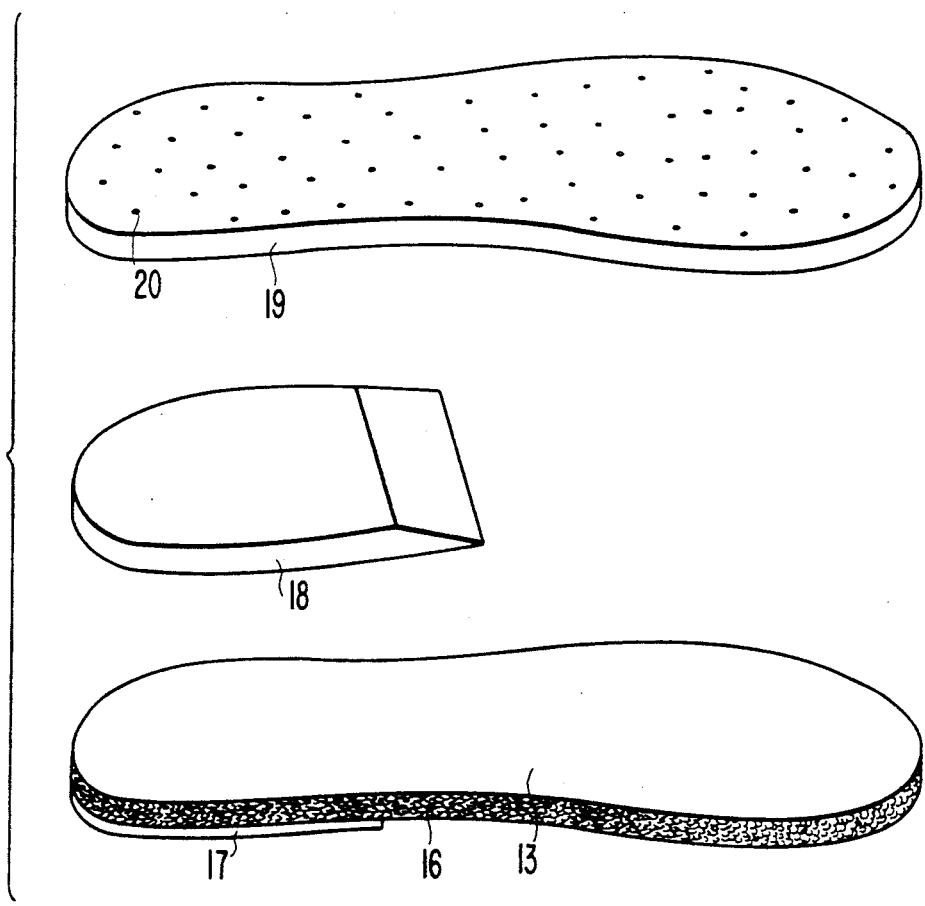
FIG. 4 is an exploded perspective view of a sole part, a heel wedge and an insert sole for a shoe bandage constructed in accordance with the present invention.

As shown in FIG. 4, the sole part 13 may, for example, be fashioned of a closed porous foam on which circumferential hook and loop fasteners 16 are externally mounted, with the fastener 16 being brought into connection with the fastening areas 14, 15 in FIG. 2. With the sole part 13 being used for a left shoe bandage, a slip-resistant shoulder 17 is secured to the lower surface of the sole 13 by, for example, a suitable adhesive such as glue. A heel wedge 18 is disposed above the sole part 13, with the heel wedge 18 being insertable into the shoe bandage and an insert sole 19, made of a soft foam with breathing openings 20, may be positioned inside the shoe bandage above the sole part 13. The insert sole 19 may have variable thickness in order to enable a better fitting of the shoe bandage.

Figure 5:
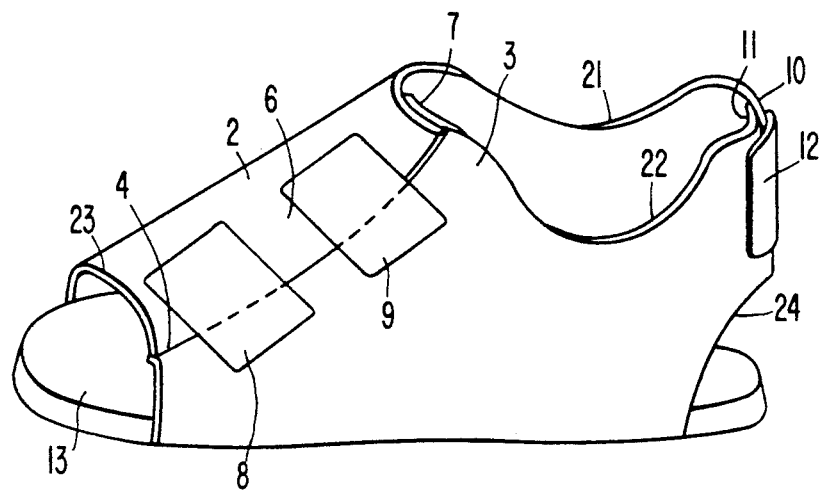
FIG. 5 is a perspective view of the shoe bandage of FIG. 3 with areas thereof cut out.

As shown in FIG. 5, cutouts 21 and 22 may be provided for accommodating the ankle, with a cutout 23 being provided for the toes and a cutout 24 for the heel. The seam 4 which holds the two halves of the upper material piece 1 is disposed above the toe cutout 23.

Figure 6:
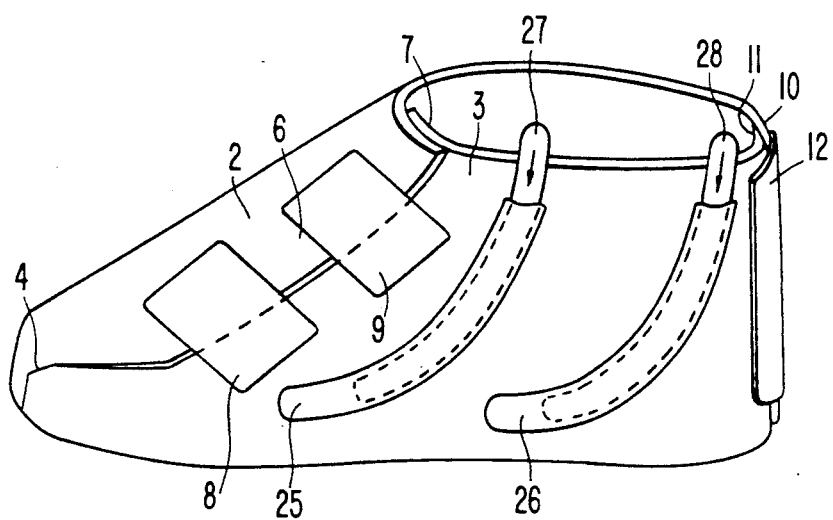
FIG. 6 is a shoe bandage according to FIG. 3 provided with reinforcing elements.

Additionally, as shown in FIG. 6, it is possible to provide two pockets 25, 26 on the outside of the shoe bandage, with the pockets 25, 26 accommodating, for example, reinforcing ribs 27, 28 insertable into the pockets 25, 26 in the direction of the arrows in FIG. 6.

Figure 7:
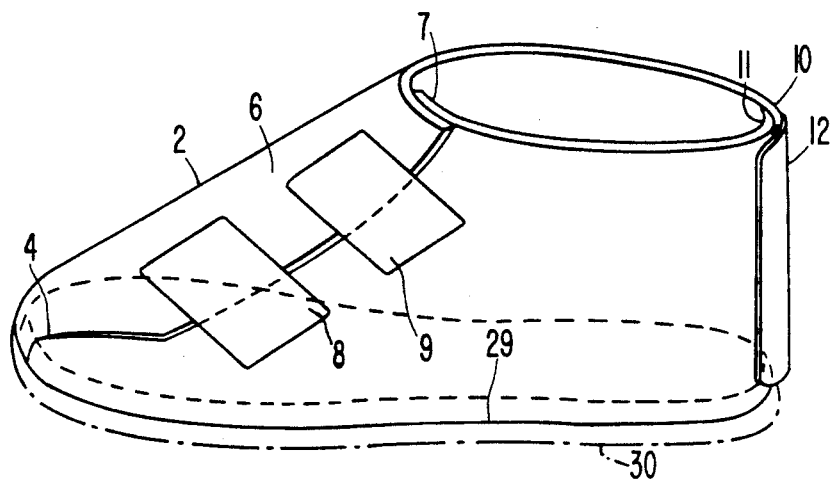
FIG. 7 is a perspective view of a completed shoe bandage constructed in accordance with the present invention with a cutout area in the upper material.

In FIG. 7, the sole part 13 is illustrated by dashed lines, with the lower edge of the upper material ends flush with the lower edge 29 of the sole, after the dot-dashed cut area has been separated from the upper material. For different foot thicknesses, a plurality of such areas can be indicated in advance by markings located side by side along the lower edge so that surplus material can be separated both before the assembly of the shoe and while the shoe is being fitted.

While I have shown and described several embodiments in accordance with the present invention, it is understood that the same is not limited thereto but is susceptible to numerous changes and modifications as known to one of ordinary skill in the art, and I therefore do not wish to be limited to the details shown and described herein, but intend to cover all such modifications as are encompassed by the scope of the appended claims.

I claim:

1. A shoe bandage adapted to be worn over foot bandages, foot injuries or foot wounds, the shoe bandage comprising:
    an upper shoe part of bandage material formed in one piece, said material of said upper shoe part, in a developed view, being flat and symmetrical, said upper shoe part including two curved sections, with a width of the two curved sections being greater in a tensioning area of the shoe bandage, and an exterior edge of the material forming a closed arc, said upper shoe part being divided in a heel area of the shoe bandage;
    a sole part provided with hook and loop fastening material surrounding an outer peripheral edge of said sole part; and
    hook and loop fastening material provided along a lower inner edge of said upper shoe part for enabling a hook and loop fastening with said sole part wherein the material of the upper shoe part, in the tensioning area, is provided with a cutout extending from an inner edge of the material to a point near an outer edge of the material.

2. A shoe bandage according to claim 1, wherein said cutout enables an overlapping of edge areas of the material in an area of the cutout, and wherein hook and loop fastening means are provided on the edge areas of said material of said upper shoe part for enabling securing of the edge areas to each other.

3. A shoe bandage according to claim 1, wherein hook and loop material members are mounted in the tensioning area and in the heel area of the shoe bandage for enabling a closing of the heel area and tensioning area.

4. A shoe bandage according to claim 3, wherein at least one cutout is provided in an ankle area of the shoe bandage.

5. A shoe bandage according to claim 4, wherein a further cutout is provided in a toe area of the shoe bandage.

6. A shoe bandage according to claim 5, wherein an additional cutout is provided in the heel area of the shoe bandage.

7. A shoe bandage according to claim 6, further comprising means provided on the upper shoe part for reinforcing the same.

8. A shoe bandage according to claim 7, wherein said means for reinforcing includes reinforcing members arranged in one of inwardly and outwardly disposed longitudinal pockets provided in the upper shoe part.

9. A shoe bandage according to claim 8, wherein said upper shoe part includes closure areas comprising a cutout portion separable from the upper shoe part for enabling an adjustment of the upper shoe part to the sole part of the shoe bandage.

10. A shoe bandage, adapted to be worn over foot bandages, foot injuries or foot wounds, the shoe bandage comprising:
    an upper shoe part of bandage material formed in one piece;
    a sole part provided with hook and loop fastening material surrounding an outer peripheral edge of said sole part; and
    hook and loop fastening material provided along a lower inner edge of said upper shoe part for enabling a hook and loop fastening with said sole part, and
    wherein the material of the upper shoe part, in a tensioning area, is provided with a cutout extending from an inner edge of the material to a point near an outer edge of the material.

11. A shoe bandage according to claim 10, wherein the material of the upper shoe part, in a developed view, includes two curved sections, a width of the two curved sections is greater in a tensioning area of the shoe bandage, and an exterior edge of the material forming the upper shoe part forms a closed arc.

12. A shoe bandage according to claim 10, wherein hook and loop material members are mounted in a tensioning area and in a heel area of the shoe bandage for enabling a closing of the heel area and the tensioning area.

13. A shoe bandage according to claim 10, wherein at least one cutout is provided in an ankle area of the shoe bandage.

14. A shoe bandage according to claim 10, wherein a further cutout is provided in a toe area of the shoe bandage.

15. A shoe bandage according to claim 10, further comprising means provided on the upper shoe part for reinforcing the same.

16. A shoe bandage according to claim 10, wherein said upper shoe part includes closure areas comprising a cutout portion separable from the upper shoe part for enabling an adjustment of the upper shoe part to the sole part of the shoe bandage.

17. A shoe bandage adapted to be worn over foot bandages, foot injuries, or foot wounds, the shoe bandage comprising:
    an upper shoe part of bandage material formed in one piece, said material, in a developed view, is flat, the material of the upper shoe part in a tensioning area is provided with a cut out extending from an inner edge of the material to a point near an outer edge of the material, said cutout enables an overlapping of edge areas of the material in an area of the cutout;
    sole part provided with hook and loop fastening material surrounding an outer peripheral edge of said sole part;
    hook and loop fastening material provided along a lower inner edge of said upper shoe part for enabling a hook and loop fastening with said sole part; and
    hook and loop fastening means provided on edge areas of said material of said upper shoe part for enabling a securing of the edge areas to each other.

* * * * *